United States Patent [19]

Abo El-Nil

[11] 4,217,730
[45] Aug. 19, 1980

[54] EMBRYOGENESIS OF GYMNOSPERM FOREST TREES

[75] Inventor: Mostafa M. Abo El-Nil, Centralia, Wash.

[73] Assignee: Weyerhaeuser Company, Tacoma, Wash.

[21] Appl. No.: 36,623

[22] Filed: May 7, 1979

[51] Int. Cl.³ .......................................... A01G 1/00
[52] U.S. Cl. ..................................................... 47/58
[58] Field of Search ............................................ 47/58

[56] References Cited

U.S. PATENT DOCUMENTS

| | | | |
|---|---|---|---|
| 3,514,900 | 6/1970 | McDade | 47/58 |
| 3,683,550 | 8/1972 | Corlett et al. | 47/58 |
| 4,152,869 | 5/1979 | Jones | 47/58 |

OTHER PUBLICATIONS

Control of Embryoid–, Al–Abta, et al., Annals of Botany, 1978, 42:773–782.
Geneticists aim to–, Chem. & Eng. News, Jun. 4, 1979, p. 26 cited.
Applications of Tissue Culture–, Plant Cell Tissue & Organ Culture, Reinert et al., 1977, pp. 93–108 cited.
Vegetative propagation–, Cheng, Plant & Cell Physiol., 1976, 17:1347–1350.
Callus formation–, Masuda et al., Phys. Plantarum, 1977, 41:135–138.
Application of Tissue–, Plant Cell & Tissue Culture Principles & Applications, Sommer et al., OSU Press, Columbus, 1979, pp. 461–491.
High Frequency induction–, Söndahl et al., Zeitschrift fur Pflanzenphysiol, 81:395–408.
In vitro embryoid–, Prop. of Higher Plants through Tiss. Cult., Wetherell NTIS, Springfield, Va., 1978, pp. 102–124.
Morphogenesis in clonal–, Winton, Frontiers of Plant Tissue Culture, Thorpe ed., Intl. Assoc. Plant Tiss. Cult., pp. 419–426.
Embryoids in–, Winton et al., Proc. TAPPI 1977 For. Biol. Wood Chem. Conf., Atlanta.
The mass production–, Winton et al., 1977, Progress Report 5, Project 3223, Inst. Paper Chemistry, Appleton.
Regeneration of –, Cheng et al., 1977, Science, 198:306–307.
Adrentive Embryony–, Halperin et al., Amer. Journ. Bot. 1964, 51:274–283.
Formation of –, Krul et al., Journ. Amer. Soc. Hort. Sci., 1977, 102:360–363.
Somatic embryogenesis–, Lörz et al., Naturwissen-Schaften, 1977, 64:439.

Primary Examiner—Robert E. Bagwill

[57] ABSTRACT

Young Douglas-fir cotyledon tissue is cultured to grow a soft callus on an agar medium containing mineral salts, organic nutrients and an auxin. No cytokinins are present except those that might be endogenous in the tissue itself. After one to two months the explants and callus are placed in a liquid suspension culture medium similar to the first in composition. Again, auxins are present and cytokinins are omitted. After about one month, bipolar embryoids have been generated in the suspension. These have chloroplasts and a vascular system with organized meristemic centers for ultimate development into stems and roots. The embryoids can be removed from the culture and placed on a growth medium for production of plantlets.

11 Claims, 1 Drawing Figure

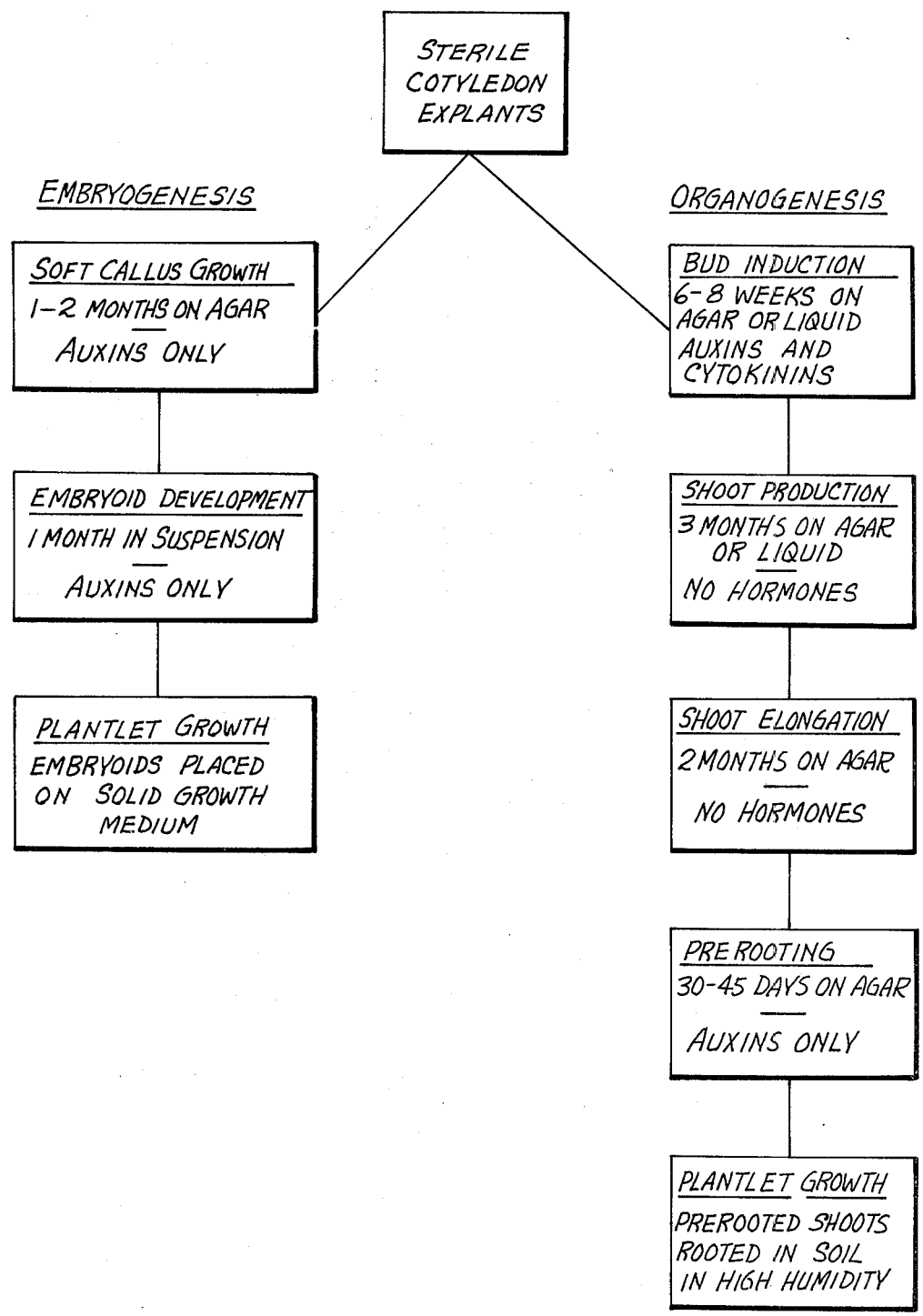

EMBRYOGENESIS OF GYMNOSPERM FOREST TREES

BACKGROUND OF THE INVENTION

The present invention relates to the reproduction of woody plant species by tissue culture techniques, and more specifically to methods utilizing suspension culture that result in embryogenesis of the cultured cells. Tissue culture has been an accepted method of reproducing a number of plant species. Commercial applications to date have largely been limited to ornamental foliage type plants; e.g., Boston fern (*Nephrolepis bostoniensis*), African violet (Saintaupaulia sp.) and various orchids. Success on woody species, particularly gymnosperms, has been much more limited and has not reached commercial stage. Nevertheless, significant progress is being made in laboratories around the world. In vitro production of plantlets has been reported for a number of commercially important American timber species; e.g., redwood (*Sequoia sempervirens*), white spruce (*Picea glauca*), longleaf pine (*Pinus palustris*), western hemlock (*Tsuga heterophylla*) and Douglas-fir (*Pseudotsuga menziesii*), as well as others [Cheng, T-Y., *Plant and Cell Physiol.* 17: 1347-50 (1976)]. Propagation of these species has not yet passed beyond the experimental stage for a number of reasons. One of the major problems, wholly aside from the principal difficulty of getting plantlets at all, has been the expense and trouble of sterile handling in the multiple steps between the explant taken from the donor and the established plantlet ready to set out in the field. The process is slow, expensive and requires a high degree of skill. These are all limitations that stand squarely in the way of the ultimate goal of mass production of genetically superior plantlets for the regeneration of cut-over or burned forest lands.

One step toward this goal is discussed in the paper by Cheng and Voqui [Science, 198: 306-307 (1977)]. The writers support the growing tissue on a porous, inert material to reduce the number of handling steps when changing culture mediums. This also enables the use of liquid mediums as opposed to agar plates. It does not, however, eliminate the need for the tedious manual dissection of adventitious buds or shoots from the growing callus mass prior to transfer to rooting medium.

Virtually all of the successful techniques to date have been based on the biological process known as organogenesis; that is the initiation of shoots from merestematic centers induced in cultured tissue explants and the subsequent rooting of these shoots. This process may generally be described in the following terms: A portion of a donor plant is excised, sterilized and placed on a growing medium. The tissue most commonly used in the woody species mentioned earlier is a portion of young cotyledon from newly sprouted seeds or the embryo dissected from a seed. A much lower degree of success has been realized when tree leaves or stem tissues are cultured.

The medium consists of a mixture of mineral salts, organic nutrients, and plant hormones. One commonly used basal medium is that of Murashige and Skoog [Physiol. Plant. 15: 473-497 (1962)]. This may be modified by addition of sucrose, myo-inositol, and thiamine [Cheng, T-Y., *Plant Science Letters*, 5: 97-102 (1975)]. Various cytokinins and auxins are also present to induce cell differentiation and growth. After an initial callus growth has formed which contains bud primordia, the plant material can be placed on a succession of different mediums that promote bud induction and shoot elongation. The shoot elongation medium may be free of hormones to reduce competing callus growth. After this stage the shoots are excised and placed in a rooting medium consisting of the basal medium with an auxin as the only hormone present. When root primordia have formed the shoots can again be nourished on a medium free of added hormones in order to encourage root growth. Ultimatly the plantlets are removed from the artificial media into a natural or synthetic soil mixture.

Another biological route to plantlets is that of embryogenesis. In this process a group of cells become organized into a bipolar embryoid which will, in a favorable environment, develop bud primordia at the upper end and root primordia at the opposite end. The normal route to production of plantlets by embryogenesis has been through suspension culture. Here the cells are suspended in a gently agitated liquid medium.

Plant reproduction by embryogenesis has been realized for only a very few plant species. It was first reported for wild carrot in suspension culture by Halperin and Wetherell [Amer. Journal of Botany 51: 274-283 (1964)] in a definitive study. Grape (Vitis sp) and coffee (Coffea sp) have also been reproduced by embryogenesis in culture [Söhndahl, M. R. and W. R. Sharp. *Z. Pflanzenphysiol. Bd.* 81: 395-408 (1977)].

One report by Winton and Verhagen (TAPPI, Forest Biology/Wood Chemistry Conference, June 20, 1977) describes the production of Douglas-fir embryoids. It must be noted their terminology differs from that generally used. They failed to achieve structures at the levels they called "embryos," which are herein referred to as "embryoids." They did find organized cell masses (which they called "embryoids") but these did not have the bipolar structure necessary for further development into plantlets and, in fact, did not continue to survive in the growth medium.

Despite the fact that studies have been carried out at a number of government and academic institutions, successful embryogenesis leading to ultimate plant production of gymnosperms has not been achieved before the present invention.

SUMMARY OF THE INVENTION

The present invention encompasses a method of production of embryoids from plants of the Subdivision Gymnospermae through the use of tissue culture in a liquid suspension. As such, it overcomes many of the problems associated with techniques of production of plantlets by organogenesis. The amount of handling is greatly reduced. This, in turn, brings the cost per plantlet to a level which is acceptable for the mass production of plantlets for reforestation. In addition, the present invention can generate huge quantities of embryoids in equipment which requires only a small space.

It is therefore an object of this invention to produce embryoids of gymnosperms that are suitable for further growth into plantlets.

It is another object to produce embryoids of gymnosperms by tissue culture in liquid suspension.

It is still a further object to produce embryoids of Douglas-fir by liquid suspension tissue culture.

These and other objects of the invention will become apparent on reading the following specification in conjunction with the attached drawings.

BRIEF DESCRIPTION OF THE DRAWINGS

The sole FIGURE is a block diagram showing typical process routes to morphogenesis resulting in the production of plantlets.

DESCRIPTION OF THE PREFERRED EMBODIMENT

A number of the botanical terms used in this patent specification are occasionally found to have different meanings in the literature. The following definitions of certain terms used in this patent specification are the ones most commonly used in the field of botany.

"Tissue culture" is the process by which tissue excised from a donor plant is nourished on a series of culture media to produce plantlets genetically identical to the donor.

A "plantlet" is a plant asexually reproduced by tissue culture.

An "embryoid" is an asexually reproduced bipolar group of organized cells having defined meristemic centers that can ultimately produce roots and foliage, together with an appropriate vascular system for internal transport of nutrients and waste products. It differs from seed embryo primarily in the asexual method of development which gives genetic identity to the tissue donor.

A "meristem" is a group of tissue-forming cells capable of further directed development into plant organs; e.g., shoots and roots.

"Adventitious" refers to organs that develop in abnormal and unpredictable locations, where orgon primodia do not normally exist.

"Morphogenesis" refers to the origin and development of organs or parts of organisms. It encompasses both organogenesis and embryogenesis. "Organogenesis" is the formation and development of organs, such as buds, from meristemic centers in tissues that would not ordinarily organize into the particular organ.

"Embryogenesis" refers to the development of embryoids from tissue that would not ordinarily organize in this manner. Embryoids are believed to develop from single plant cells as a result of a particular hormonal/nutritional regimen.

An "explant" is a piece of tissue taken from a donor plant for culturing.

"Callus" is a growth of unorganized and either unconnected or loosely connected plant cells normally produced from culturing an explant.

"Cytokinins" are plant hormones that effect the organization of dividing cells and function in the transmission of information from DNA for protein formation.

"Auxins" are plant hormones that promote cell division and growth.

Other definitions of terms that might be ambiguously construed will be given when the term is first used.

Throughout this description, the extremely critical importance of plant hormones must be kept in mind. Factors of presence or absence of a specific hormone, concentrations, and the synergistic or deleterious effects of combinations of hormones are largely unpredictable in their effect. These materials are effective in minute concentrations normally measured in the micromole ($\mu$m = $10^{-6}$ mole) to nanomole (nm = $10^{-9}$ mole) range.

The example given will refer to Douglas-fir (*Pseudotsuga menziesii*) but it should be noted that the same general process should be suitable for other members of the family Pinaceae. In particular, it would be expected that the southern yellow pines should respond well to the present process. These include loblolly pine (*Pinus taeda*), slash pine (*Pinus elliotii*) longleaf pine (*Pinus palustris*), and shortleaf pine (*Pinus echinata*). Another species which has responded well to tissue culture by organogenesis and should be equally responsive to the present method is western hemlock (*Tsuga canadensis*).

The present process, and how it differs from apparently similar work in the prior art, can be demonstrated by reference to the FIGURE. Both of these will be described in detail so that the differences between them will be apparent.

For either the embryogenesis or organogenesis routes, Douglas-fir seeds are conventionally germinated in moist soil. Cotyledon clusters are then excised from the seedlings at the hypocotyl two to four weeks after planting, depending somewhat on germination time. Three weeks after planting is preferred. These are sterilized by first washing in a solution of three percent Alconox (granular laboratory glassware detergent, trademark of Alconox, Inc., New York, N.Y.) and 0.5 percent Tween-20 (polyoxyethylene sorbitan monolaurate, a nonionic surfactant, trademark of ICI Americas, Inc., Wilmington, Del.) with gentle agitation. Many other equally suitable surfactants are well known to those skilled in the art. The cleaning solution is decanted off and replaced with a solution of 50 percent household bleach (5.25 percent sodium hypochlorite) and 50 percent water which contained 0.1 percent Alconox (w/v) and 0.5 percent Tween-20 (v/v) for about six minutes. Excellent results are obtained by sterilizing about 150 complete colytedon clusters in one liter of sterilant. The bleach is drained off and the cotyledons are gently washed in five exchanges of sterile deionized water. The sterilized cotyledons are then cut into 5 mm long sections for culturing. Three to four explants are obtained from each cotyledon.

A basal solution for all of the subsequent culturing is prepared by the method of Murashige and Skoog, referred to earlier. Stock solutions are prepared at 200× concentration except B, below, which is stored at 100× concentration; thus 5 mL of the 200× material or 10 mL of the 100× material is used for every liter of actual full-strength basal salt solution, hereafter designated as MS solution.

TABLE I

| Stock Solution Designation | Compounds | Stock Solution Concentration g/L | Final Medium Concentration mg/L |
| --- | --- | --- | --- |
| A | NH$_4$NO$_3$ | 330.0 | 1650.0 |
|   | KNO$_3$ | 190.0 | 1900.0 |
| B | H$_3$BO$_3$ | 1.24 | 6.2 |
|   | KH$_2$PO$_4$ | 34.0 | 170.0 |
|   | KI | 0.166 | 0.83 |
| C | Na$_2$MoO$_4$ . 2HOH | 0.05 | 0.25 |
|   | CoCl$_2$ . 6HOH | 0.005 | 0.025 |
|   | CaCl$_2$ . 2HOH | 88.0 | 440.0 |
| D | MgSO$_4$ . 7HOH | 74.0 | 370.0 |
|   | MnSO$_4$ . 4HOH | 4.46 | 22.3 |
|   | ZnSO$_4$ . 7HOH | 1.72 | 8.6 |
| E | CuSO$_4$ . 5HOH | 0.005 | 0.025 |
|   | Na$_2$EDTA | 7.45 | 37.25 |
| F | FeSO$_4$ . 7HOH | 5.57 | 27.85 |

Six culture media were prepared by the following formulations. Media A through D are used for production of plantlets by organogenesis while Media E and F are used for production of embryoids. Formulations for these are given in Table 2.

TABLE 2

| Composition[10] | Culture Media Medium | | | | | |
|---|---|---|---|---|---|---|
| | A | B | C | D | E | F |
| MS Solution[1] | ½X | ½X | ½X | ¼X[2] | 1X | 1X |
| thiamine, mg/L | 2.4 | 2.5 | 2.5 | 2.5 | 2.5 | 2.5 |
| myo-inositol, mg/L | 250 | 250 | 250 | 250 | 250 | 250 |
| sucrose, g/L | 30 | 10 | 10 | — | 30 | 30 |
| nutrient broth / g/L[3] | 1 | — | — | — | — | — |
| BAP, mg/L[4] | 1.0 | — | — | — | — | — |
| IAA, mg/L[5] | 1.0 | — | — | — | — | — |
| IBA, mg/L[6] | 1.0 | — | — | 3.0 | — | — |
| NAA, mg/L[7] | — | — | — | 0.01 | 1.0 | — |
| 2,4-D, mg/L[8] | — | — | — | — | — | 1.0 |
| Agar, g/L | — | — | 6 | 6 | (6)[9] | (6)[9] |

[1] ½X designates half strength, etc.
[2] MS solution for Medium D was ¼X for components B, C, D, E and F and full strength for component A.
[3] Difco dehydrated nutrient broth; Difco Laboratories; Detroit, Michigan.
[4] $N_6$-benzylaminopurine - cytokinin
[5] indol-3-acetic acid
[6] indole-3-butyric acid  } auxins
[7] naphthalene-2-acetic acid
[8] 2,4-dichlorophenoxyacetic acid
[9] Media E' and F' were made without agar.
[10] All media were adjusted to pH 5.5 with HCl or NaOH.

EXAMPLE 1

Looking now at the production of plants by organogenesis, an example will be given using the general technique of Cheng and Voqui, cited earlier, in which the explants are cultured on a polyester support. It should be understood that the same mediums would give comparable results using agar plates. One support material which has worked well is Poly-fil quit batting (Fairfield Processing Co., Danbury, Conn.). This is a light-weight, porous felt comprising all polyester fibers without binder, weighing about 100 g/m².

The support felt is first cut into discs to fit easily into 80×25 mm plastic petri dishes. Twenty felt discs and 500 mL of Medium A are autoclaved for eight minutes at 121° C. to destroy contaminants. A similar sterilization schedule was used for all of the culture media. The discs are transferred to the sterile petri dishes with approximately 20 mL of the bud induction medium (Medium A). Approximately 25 sterilized cotyledon explants are placed on the surface of the felt in contact with the liquid medium. The dishes are covered and sealed. This first stage of culturing is for a period of about 45 days at 21° C. in a 16-hour light and 8-hour dark schedule. There may be a minor growth of callus tissue on the cut ends but this will not be extensive. The surfacr of the explants will have developed a number of small knobby structures (meristemoids) that will ultimately develop into bud meristems.

The next stage is to aspirate as much of the initial medium from the dish as possible. From 80 percent to 90 percent can be easily removed. This is replaced with sterile Medium B which is a shoot production material lacking any plant hormones. The meristemoids observed earlier will develop into short shoots about five to ten millimeters long. Culturing conditions are the same as before with a 16-hour light and 8-hour dark period at 21° C., typically for about 90 days.

When the shoots have reached the above size they are excised from the mass and transferred individually into sterile Medium C on agar plates. About 25 adventitious shoots can be grown in an 8 cm diameter petri dish using an agar layer about 8 mm deep. Growth conditions similar to the above are maintained for about two months until the shoots are about 20–25 mm high. At this point no roots have yet developed.

Two paths are open to further development. The shoots may either be placed directly in unsterile soil to allow rooting or they may be transferred to a fourth medium for a prerooting treatment. Use of the latter treatment gives a somewhat higher success rate. It consists of a 30 to 45 day period in Medium D under similar growth conditions to those described before. The shoots, still normally without visible roots, are then transplanted into soil and maintained for several weeks at or near 100 percent relative humidity until full rooting has occurred.

The success rate of achieving rooted plantlets from shoots varies between about 15 percent to over 50 percent depending on the genetic background of the original seed. Explants taken from wild seed average about 35 percent successful plantlets from cultured shoots.

EXAMPLE 2

Embryogenesis of Douglas-fir can be achieved by the following procedure: The sterile cotyledon explants prepared as in Example 1 are cultured on agar plates using either Medium E or F. About 20–25 mL of the medium is used in 80×15 mm petri dishes. It should be noted that in contrast to the original medium used before, Medium E contains no cytokinins. This is quite at odds with the usual understanding as to how woody plants should be cultured although some soft-tissued noneconomic plants, such as wild carrot, have been cultured by an auxin only route.

After a culturing period of one to two months at 21° C. with the same 16-hour light and 8-hour dark cycle as in the previous example, the explants will normally have split longitudinally and a granular callus will have formed in the split area. The entire mass is lifted off of the agar and placed in a liquid medium which may be either Medium E' or F' without any agar. About five of the explant/callus masses are placed in 25 mL of the medium in a 250 mL capped Erlenmeyer culture flask or two such masses may be placed in 10 mL of medium in a capped 50 mL test tube. Sterile conditions of equipment, media and handling must naturally be observed. It should be particularly noted that any severe mechanical treatment to break up the callus is undesirable and may even be fatal to further success. The callus should not be screened to remove the remaining portions of the explant or other tissues. This is again in opposition to the teachings of the prior art.

The flask and test tube suspension cultures are equally suitable and differ only in scale. Both methods will be briefly described. The suspension flasks are placed on a shaker table giving gentle agitation at 100 rpm. The test tubes are placed in racks at about a 15° inclination from the horizontal and the racks are rolled at one rpm. Temperature and photoperiod are as described before. The callus mass will readily break up under these conditions so as to allow embryogenesis to take place.

After about one month the connective tissue and much of the callus mass will have become dark brown or gray and will be either senescent or dead. Among this unpleasant-appearing suspension will be numbers of small whitish embryoids about 0.3 to 1.5 mm in diameter. These are bipolar bodies having the general shape of small light bulbs or ellipsoids. One end will show green chloroplasts in an apparent bud meristem while the other end will exhibit the characteristics of an incipient radicle. Even larger embryoids, two to three millimeters in diameter, can be attained by culturing the suspensions at 5° C. to 8° C. in an environment with greatly reduced light intensity.

The embryoids from the suspension culture may be withdrawn and placed on any suitable nutrient medium for further development into plantlets, much in the fashion of an embryo removed from the endosperm of the seed.

If it is desired to maintain embryoids in suspension culture for any period of time this may be done by changing the medium on approximately a monthly basis and substituting fresh medium E' or F'. In this way living genetic material can be maintained for long periods of time.

The concentration of auxins in the medium will be rather critical but a range between 0.1 and 2.0 mg/L of the auxin will give satisfactory results. The optimum value will depend somewhat on the characteristics of the individual auxin used. For NAA and 2,4-D this appears to be about 1.0 mg/L. For NAA this corresponds to about 5.4 µm and for 2,4-D about 4.5 µm. It appears to be essential that both the callus growth medium and suspension medium contain some auxin without any cytokinins other than those that might be endogeneous in the tissue itself.

I claim:

1. A method of generating embryoids from tissues of Douglas-fir (*pseudotsuga menziesii*) trees by plant tissue culture which comprises:
   a. excising tissue from a donor plant;
   b. culturing the excised tissue on a first medium containing mineral and organic nutrients and auxins as the sole exogenous plant hormone until a soft callus tissue has developed;
   c. transferring the callus without significant mechanical disintegration into a suspension medium containing similar nutrient and hormone materials to the first medium, this medium also having auxins as the sole exogenous plant hormone; and
   d. agitating the suspension gently so as to permit bipolar embryoids to differentiate and develop.

2. The method of claim 1 including the additional step of removing the embryoids from the suspension and placing them on a solid growth medium for development into plantlets.

3. The method of claim 1 where the tissue is taken from cotyledons two to four weeks after seed planting.

4. The method of claim 1 where the auxins are selected from the group consisting of 2,4-dichlorophenoxyacetic acid, naphthalene-2-acetic acid, indole-3-acetic acid, indole-3-butyric acid or mixtures thereof.

5. The method of claim 4 where the auxin is 2,4-dichlorophenoxyacetic acid.

6. The method of claim 4 where the auxin is naphthalene-2-acetic acid.

7. The method of claim 4 where the auxins are present in a concentration of 0.1 to 2.0 mg/L of medium.

8. The method of claim 1 where the tissue is maintained on the first medium for a period that does not exceed two months.

9. The method of claim 1 where the photoperiod is 16 hours of light and 8 hours of darkness for both mediums.

10. The method of generating plantlets from tissues of trees of Douglas-fir (*Pseudotsuga menziesii*) by tissue culture which comprises:
    a. excising tissue from a donor plant;
    b. culturing the excised tissue on a first medium containing mineral salts, organic nutrients, and an auxin selected from the group consisting of 2,4-dichlorophenoxyacetic acid and naphthalene-2-acetic acid or mixtures thereof in a concentration of from 0.1 to 2.0 mg/L, for a period from one to two months until a soft callus has formed;
    c. transferring the callus without significant mechanical disintegration to a second medium which is a liquid and in which the callus is suspended by gentle agitation, the second medium being similar to the first medium in chemical composition, until bipolar embryoids have formed; and
    d. removing the embryoids and placing them on a solid growth medium until plantlets have formed.

11. The method of claim 10 in which the tissue cultured is two to four week old cotyledon tissue.

* * * * *